(12) United States Patent
Guenther

(10) Patent No.: US 12,099,106 B2
(45) Date of Patent: Sep. 24, 2024

(54) ARTERIAL SPIN LABELING WITH EVALUATION OF INVERSION STATE OF MAGNETIZATION

(71) Applicant: Fraunhofer-Gesellschaft zur Foerderung der angewandten Forschung eingetragener Verein, Munich (DE)

(72) Inventor: Matthias Guenther, Bremen (DE)

(73) Assignee: Fraunhofer-Gesellschaft zur Foerderung der angewandten Forschung eingetragener Verein, Munich (DE)

( * ) Notice: Subject to any disclaimer, the term of this patent is extended or adjusted under 35 U.S.C. 154(b) by 535 days.

(21) Appl. No.: 17/052,190

(22) PCT Filed: May 6, 2019

(86) PCT No.: PCT/EP2019/061592
§ 371 (c)(1),
(2) Date: Nov. 1, 2020

(87) PCT Pub. No.: WO2019/211493
PCT Pub. Date: Nov. 7, 2019

(65) Prior Publication Data
US 2021/0124000 A1     Apr. 29, 2021

(30) Foreign Application Priority Data

May 4, 2018   (DE) .................... 10 2018 110 826.5

(51) Int. Cl.
*G01R 33/563* (2006.01)
*A61B 5/055* (2006.01)
*G01R 33/56* (2006.01)

(52) U.S. Cl.
CPC ........ *G01R 33/56366* (2013.01); *A61B 5/055* (2013.01); *G01R 33/5602* (2013.01); *G01R 33/56308* (2013.01)

(58) Field of Classification Search
CPC .......... G01R 33/56366; G01R 33/5602; G01R 33/56308; A61B 5/055
See application file for complete search history.

(56) References Cited

U.S. PATENT DOCUMENTS 8,260,396 B2   9/2012  Guenther
2008/0269595 A1*  10/2008  Wong .................... A61B 5/055
                                                              600/419

(Continued)

FOREIGN PATENT DOCUMENTS

CN        1685243 A      10/2005
CN      103748478 A       4/2014

(Continued)

OTHER PUBLICATIONS

Chen, Z., et al., "Simultaneous Measurement of Brain Perfusion and Labeling Efficiency in Single Pseudo-Continuous Arterial Spin Labeling Scan," Magnetic Resonance in Medicine. vol. 79, 2017. p. 1922-1930 (Year: 2017).*

(Continued)

*Primary Examiner* — Sean A Frith
(74) *Attorney, Agent, or Firm* — Lowe Graham Jones, PLLC; Ellen M. Bierman

(57) ABSTRACT

An MRI system and method for generating MR images is provided. An MR signals acquisition unit is configured to generate a main magnetic field, orienting the magnetization of blood within a subject, and first inversion/non-inversion RF pulses such that predetermined sequences of blood boli with inverted/non-inverted magnetization are generated. First inversion/non-inversion MR signals can be acquired, which are caused by the influence on the magnetization by (Continued)

the first inversion/non-inversion RF pulses. MR images may be generated by an image generation unit based on imaging MR signals, acquired after the sequences of inverted and non-inverted blood boli have been flowed from the first region to the part to be imaged, and the predetermined sequences. An evaluation unit is configured to evaluate the inverting of the magnetization in the first region based on the first inversion and/or non-inversion MR signals. In one embodiment, the labeling efficiency of a pseudo continuous arterial spin labeling (pCASL) MRI experiment is performed.

18 Claims, 15 Drawing Sheets

(56) References Cited

U.S. PATENT DOCUMENTS

| | | | |
|---|---|---|---|
| 2012/0271157 A1* | 10/2012 | Wong | A61B 5/0042 600/419 |
| 2015/0309147 A1* | 10/2015 | Schmitter | G01R 33/443 600/410 |
| 2016/0203603 A1* | 7/2016 | Li | G01R 33/56366 382/131 |
| 2017/0160365 A1 | 6/2017 | Helle et al. | |
| 2018/0180697 A1 | 6/2018 | Samson-Himmelstjerna et al. | |
| 2019/0053735 A1* | 2/2019 | Hu | A61B 5/055 |

FOREIGN PATENT DOCUMENTS

| | | |
|---|---|---|
| CN | 104919330 A | 9/2015 |
| DE | 102014205789 | 10/2015 |
| DE | 102016206724 | 10/2017 |
| WO | 2007/003582 | 1/2007 |

OTHER PUBLICATIONS

Wu, W., et al., "Pseudocontinuous arterial spin labeling perfusion magnetic resonance imaging—A normative study of reproducibility in the human brain," NeuroImaging. vol. 56, 2011. p. 1244-1250 (Year: 2011).*

Chen, Z., et al., "Measuring the Labeling Efficiency of Pseudocontinuous Arterial Spin Labeling," Magnetic Resonance in Medicine. vol. 77, 2017. p. 1841-1852 (Year: 2017).*

Shin, D., et al., "Pseudocontinuous Arterial Spin Labeling with Optimized Tagging Efficiency," Magnetic Resonance Medicine. vol. 68(4), 2012. p. 1135-1144 (Year: 2012).*

Dai, W., et al., "Continuous Flow Driven Inversion for Arterial Spin Labeling Using Pulsed Radiofrequency and Gradient Fields," Magnetic Resonance in Medicine. vol. 60(6), 2008. p. 1488-1497 (Year: 2008).*

Jung, Y., et al., "Multiphase Pseudocontinuous Arterial Spin Labeling (MP-PCASL) for Robust Quantification of Cerebral Blood Flow," Magnetic Resonance in Medicine. vol. 64, 2010. p. 799-810 (Year: 2010).*

Aslan, S. et al., "Estimation of Labeling Efficiency in Pseudocontinuous Arterial Spin Labeling," Magnetic Resonance in Medicine 63:765-771 (2010).

Chen, Z. et al., "Simultaneous Measurement of Brain Perfusion and Labeling Efficiency in a Single Pseudo-Continuous Arterial Spin Labeling Scan," Magnetic Resonance in Medicine 79:1922-1930 (2018).

Dai, W. et al., "Continuous Flow-Driven Inversion for Arterial Spin Labeling Using Pulsed Radio Frequency and Gradient Fields," Magnetic Resonance in Medicine 60:1488-1497 (2008).

Datta, A. et al., "Mitigation of Near-Band Balanced Steady-State Free Precession Through-Plane Flow Artifacts Using Partial Dephasing," Magnetic Resonance in Medicine, 2017, 10 pages.

Deshmane, A. et al., "Parallel MR Imaging," J. of Magnetic Resonance Imaging 36:55-72 (2012).

Detre, J. et al., "Perfusion Imaging," Magnetic Resonance in Medicine 23, 37-45 (1992).

Englund, E. et al., "Experimental assessment of pCASL labeling efficiency in the peripheral vasculature," Proc. Intl. Soc. Mag. Reson. Med. 23 (2015), p. 2342.

Guenther, M., "Arterial Spin Labeled Input Function (ASLIF); signal acquisition during pseudo-continuous arterial spin labeling," Proc. Intl. Soc. Mag. Reson. Med. 26 (2018), 5 pages.

Guenther, M., "Highly efficient accelerated acquisition of perfusion inflow series by Cycled Arterial Spin Labeling," Proc. Intl. Soc. Mag. Reson. Med. 15 (2007), p. 380.

Hargreaves, B., "Rapid Gradient-Echo Imaging," J. of Magnetic Resonance Imaging 36:1300-1313 (2012).

International Search Report and Written Opinion of the International Searching Authority completed Jul. 23, 2019, in International Patent Application No. PCT/EP2019/061592, 14 pages.

Markl, M., "Velocity Encoding and Flow Imaging," University Hospital Freiburg, Dept. of Diagnostic Radiology, Medical Physics, Freiburg, Germany, 2006, 10 pages.

Mulkern, R., "In-Plane Spatial Encoding in MRI and its Central Role in Determining Contrast and Artifact with RF Echo Planar Techniques," Concepts in Magnetic Resonance, 1992, 4, 307-325.

Peeters, F., "Interpretation of Flow Encoding and Quantification in MRI: Time Domain Versus Frequency Domain," MRM 36:758-766 (1996).

Shin, D. et al., "Pseudocontinuous Arterial Spin Labeling with Optimized Tagging Efficiency," Magnetic Resonance in Medicine 68:1135-1144 (2012).

Von Samson-Himmelstjerna, F. et al., "Walsh-Ordered Hadamard Time-Encoded Pseudocontinuous ASL (WH pCASL)," Magnetic Resonance in Medicine 76:1814-1824 (2016).

Williams, D. et al., "Magnetic resonance imaging of perfusion using spin inversion of arterial water," Proc. Natl. Acad. Sci. USA vol. 89, pp. 212-216, Jan. 1992.

Wu, W. et al., "Pseudocontinuous arterial spin labeling perfusion magnetic resonance imaging—A normative study of reproducibility in the human brain," Neuroimage 56 (2011) 1244-1250.

International Search Report issued in corresponding Chinese Application No. 201980030328.9, on Apr. 29, 2024, plus English Translation, 4 pages.

* cited by examiner 1, 2, 3, 4, 5, 6, 7, 8,
9, 10, 11, 12, ...

ARTERIAL SPIN LABELING WITH EVALUATION OF INVERSION STATE OF MAGNETIZATION

CROSS-REFERENCE TO RELATED APPLICATIONS

This application is a U.S. national phase of International Patent Application No. PCT/EP2019/061592 filed May 6, 2019; which claims priority from Germany Patent Application No. 10 2018 110 826.5 filed May 4, 2018, the contents of which are incorporated herein by reference in their entireties.

TECHNICAL FIELD

The invention relates to a magnetic resonance imaging (MRI) system, method and computer program.

BACKGROUND

In clinical diagnostics or in biomedical research the determination of hemodynamic parameters like blood volume, permeability, and blood flow (perfusion) is of great relevance to acquire information about the status and functionality of tissue and organs. For many applications one of the most important parameters is the perfusion of the blood in a tissue of interest.

In medical imaging different methods are used to determine this parameter. For instance, for measuring the blood flow within a tissue of interest a contrast agent can be injected into the blood system of a patient and several images of the tissue of interest can be acquired at different points in time. From the acquired images showing the distribution of the contrast agent in the tissue at different time points the perfusion, dynamics and kinetics of the blood can be determined.

Instead of injecting a contrast agent, like for instance Gadolinium, non-invasive contrast techniques can be used, in which an endogenous contrast agent like the blood of the patient is utilized. One of these non-invasive techniques that allow for a time resolved measurement of the blood flow in a tissue of interest is arterial spin labeling (ASL). ASL has the advantage that there is no need for injecting any contrast agent in an artery or in a vein as is a requirement for almost all other methods which measure regional perfusion. The basic idea of ASL is to label inflowing blood water spins by inverting their magnetization upstream of an imaging region. To reliably cancel out a magnetic resonance signal of stationary spins within the imaging region, a control experiment is formed where the magnetization of inflowing spins is not inverted. The labeled blood water signal is then yielded by subtraction.

In general, ASL preparation and image readout can be separated. Therefore, known methods improving ASL preparation can typically be used with any existing readout technique, wherein ASL preparation schemes can be divided into two groups. The first group is pulsed ASL (PASL) where the blood is labeled in a short amount of time (typically 10 ms) and in a large region (e.g. 5 to 10 cm thick slab). The second group labels blood in a small region, but over a long period of time (up to several seconds). This is called continuous ASL (CASL). The first CASL methods utilized a continuous radio frequency pulse (RF pulse), which will in the presence of an appropriate magnetic field gradient perform so-called flow-driven adiabatic inversion of flowing spins. The continuous application of RF power is a large demand to an MR system, which limits stability and usability of the method. An improvement of this classical CASL preparation is the pseudo CASL approach (pCASL), where the continuous application of RF is split up into several short RF pulses, which can be named labeling RF pulses, and which are separated by gaps, which can be named inter-RF gaps. Typical numbers are a 500 µs duration of the RF labeling pulse and a 500 µs gap, yielding a RF repetition rate of one per ms.

A major drawback of CASL techniques including pCASL is that the flow-driven adiabatic inversion process is sensitive to, for instance, local magnetic field inhomogeneities. This can lead to the result that not the complete magnetization of the blood flowing in the vessels can be inverted but portions of it. The fraction of inverted blood is called inversion efficiency and is a very important parameter when it comes to flow quantification. Variations in inversion efficiency in different vessels will lead to wrong perfusion estimates in different regions of the brain, i.e. in the corresponding vascular territories, which can have critical impact on diagnostic interpretations of the measurement. Therefore, it is important to know labeling efficiency, i.e. inversion efficiency, on an individual basis.

The inversion efficiency can be measured by performing experiments which compare the inverted amount of magnetization with the fully relaxed magnetization, which can be called M0. The difference between label and control experiments in ASL is divided by 2 times M0 to yield labeling efficiency. This has been demonstrated in some publications, for instance in the article "Estimation of labeling efficiency in pseudocontinuous arterial spin labeling" by S. Asian et al., Magnetic Resonance in Medicine, 63(3), pages 765 to 771 (2010), which is herewith incorporated by reference, and was compared to simulations which showed good agreement.

However, these experiments are done in addition to the conventional ASL measurement, thus increasing scan time. Therefore, labeling efficiency is not measured in each subject on a regular basis. To reduce the effect of local magnetic field inhomogeneity, additional actions are taken, like shimming, to at least correct for linear field changes, but this takes additional time and is error prone because it does not work automatically. All this is an obstacle for reliability and robustness of pCASL.

BRIEF SUMMARY

It is an object of the present invention to provide an MRI system, method and computer program which allow for a very fast evaluation of the inversion of the magnetization.

In a first aspect of the present invention an MRI system for generating an MR image of a part of a subject is provided, wherein the MRI system comprises:
an MR signals acquisition unit constructed for acquiring MR signals of a subject, wherein the MR signals acquisition unit is constructed to:
generate a main magnetic field that orients the magnetization of blood within the subject,
be operated in a) an inversion state in which first inversion RF pulses for inverting the magnetization in a first region, which is, with respect to the blood flow, upstream of the part to be imaged, are generated, and b) a non-inversion state in which first non-inversion RF pulses for non-inverting the magnetization in the first region are generated, wherein the first inversion and non-inversion RF pulses are generated such that predetermined sequences of inverted and non-inverted blood boli with inverted and non-inverted, respectively, magnetization are generated, which flow from the first region to the part to be imaged, wherein first inversion magnetic resonance signals are acquired, which are caused by the influence of the magnetization by the first inversion radio frequency pulses, and/or first non-inversion magnetic resonance signals are acquired, which are caused by the influence of the magnetization by the first non-inversion radio frequency pulses, and acquire imaging MR signals at the part to be imaged, after the sequences of inverted and non-inverted blood boli have been flowed from the first region to the part to be imaged, an image generation unit constructed for generating an MR image of the part to be imaged based on the acquired imaging MR signals and the predetermined sequences, and an evaluation unit constructed for generating an evaluation result by evaluating the inverting of the magnetization in the first region based on the acquired first inversion MR signals and/or the acquired first non-inversion MR signals.

In a further aspect of the present invention an MR imaging method for generating an MR image of a part of a subject is presented, wherein the MR imaging method comprises:

generating a main magnetic field that orients the magnetization of blood within the subject by using an MR signals acquisition unit, operating the MR signals acquisition unit in a) an inversion state, in which first inversion RF pulses for inverting the magnetization in a first region, which is, with respect to the blood flow, upstream of the part to be imaged, are generated, and b) a non-inversion state in which first non-inversion RF pulses for non-inverting the magnetization in the first region are generated, wherein the first inversion and non-inversion RF pulses are generated such that predetermined sequences of inverted and non-inverted blood boli with inverted and non-inverted, respectively, magnetization are generated, which flow from the first region to the part to be imaged, wherein first inversion magnetic resonance signals are acquired, which are caused by the influence on the magnetization by the first inversion radio frequency pulses, and/or first non-inversion magnetic resonance signals are acquired, which are caused by the influence on the magnetization by the first non-inversion radio frequency pulses, generating an evaluation result by evaluating the inverting of the magnetization in the first region based on the acquired first inversion MR signals and/or the acquired non-inversion MR signals by an evaluation unit, acquiring imaging MR signals at the part to be imaged, after the sequences of inverted and non-inverted blood boli have been flowed from the first region to the part to be imaged, by the MR signals acquisition unit, generating an MR image of the part to be imaged based on the acquired imaging MR signals and the predetermined sequences by an image generation unit.

In a further aspect of the present invention a computer program is presented, wherein the computer program comprises program code means for causing an MRI system as defined in claim 1 to carry out the steps of the MR imaging method as defined in claim 16, when the computer program is run on a computer controlling the MR imaging system.

It shall be understood that the MRI system of claim 1, the MRI method of claim 16 and the computer program of claim 17 have similar and/or identical preferred embodiments as defined in the dependent claims.

It shall be understood that a preferred embodiment of the invention can also be any combination of the dependent claims with the respective independent claim.

DETAILED DESCRIPTION

Figure 1:
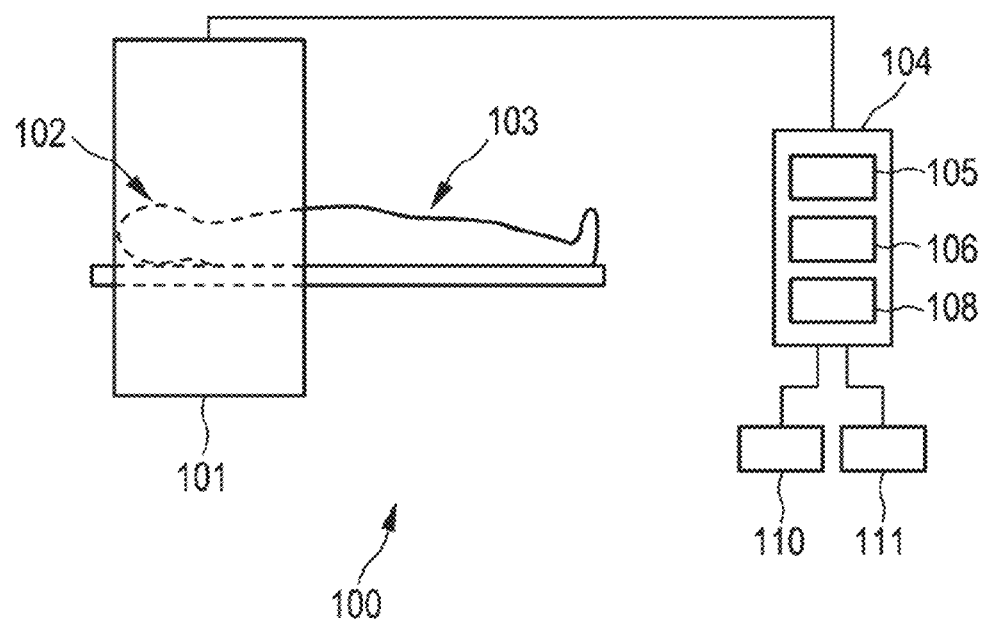
FIG. 1 shows schematically and exemplarily an embodiment of an MRI system for generating an MR image of a subject.

The MRI system is preferentially adapted to perform pCASL MRI, wherein the first inversion RF pulses are labeling pulses in pCASL for inverting the magnetization in the first region, which could also be regarded as being a labeling region. The labeling pulses in pCASL are used to invert the magnetization of flowing hydrogen spins. At the same time, they can also be viewed as excitation pulses, thus, yielding transverse magnetization, which can be measured, i.e. which results in the first inversion MR signals. Neighboring first non-inversion RF pulses are preferentially shifted by a phase of 180 degrees such that they do substantially not invert the magnetization. However, also these first non-inversion RF pulses can be viewed as excitation pulses yielding transverse magnetization which can be measured, i.e. which results in the first non-inversion signal. These magnetizations can be utilized to evaluate the quality of inversion. The result of the evaluation is preferentially an inversion efficiency, i.e. a labeling efficiency.

Thus, the detection of the first MR signals preferentially allows the measurement of the longitudinal magnetization in a pCASL sequence at the time of labeling and non-labeling. Therefore, labeling efficiency can be estimated with high temporal resolution and if needed spatially resolved, allowing for the estimation of, for instance, labeling efficiency in individual vessels. The measurement does not add to the scan time of a pCASL experiment and in its simplest form does not add anything else but additional signal readouts.

The first inversion RF pulses modify the longitudinal magnetization, wherein the longitudinal axis is defined by the generated main magnetic field. This inversion of the magnetization in the first region by the first inversion RF pulses also creates a transverse magnetization which is proportional to the original longitudinal magnetization right before the application of each inversion RF pulse, wherein the proportionality factor is $\sin(\alpha_{RF})$. Its argument $\alpha_{RF}$ denotes the tip angle, also called flip angle, of each of the first inversion RF pulses. The first inversion MR signals are indicative of the transverse magnetization, i.e. the evaluation unit is adapted to determine the transverse magnetization based on the first inversion MR signals, and to use the determined transverse magnetization to determine the original longitudinal magnetization and hence the amount of labeled blood magnetization which will eventually flow into the part to be imaged. The amount of labeled blood magnetization entering a voxel of an imaging region, in which the part to be imaged can be present, can be called input function. The entire technique can therefore be called arterial spin labeled input function (ASLIF).

Also the first non-inversion RF pulses modify the longitudinal magnetization, wherein the longitudinal axis is defined by the generated main magnetic field. This inversion of the magnetization in the first region by the first non-inversion RF pulses also creates a transverse magnetization which is proportional to the original longitudinal magnetization right before the application of each inversion RF pulse, wherein the proportionality factor is $\sin(\alpha_{RF})$. The sign of the tip angle $\alpha_{RF}$ changes from first non-inversion RF pulse to first non-inversion RF pulse such that the magnetization is flipped back and forth. This leads to the non-inversion signal, but the net change in the orientation of the magnetization is zero. This is in contrast to the first inversion RF pulses, which flip the magnetization always in the same direction, in order to invert the magnetization.

The MR signals acquisition unit is therefore preferentially adapted to provide a pCASL MR sequence which acquires MR data at the time of labeling. In pCASL this can be done by including a signal readout, which can be named analog-to-digital-conversion (ADC) event, between single labeling pulses, i.e. in the corresponding inter-RF spacings of the pCASL MR sequence.

The first inversion magnetic resonance signals and the first non-inversion magnetic resonance signals are acquired during the time period in which the first inversion radiofrequency pulses invert and the first non-inversion radiofrequency pulses do not invert the magnetization in the first region, respectively. In particular, several first inversion radiofrequency pulses are used for generating an inverted blood bolus in the first region, wherein for acquiring a first inversion magnetic resonance signal a signal readout is temporally located in between two first inversion radiofrequency pulses. Correspondingly, several first non-inversion radiofrequency pulses are used for generating a non-inverted blood bolus in the first region, wherein for acquiring a first non-inversion magnetic resonance signal a signal readout is temporally located in between two first non-inversion radiofrequency pulses. Thus, as explained above, the acquisition of the first inversion magnetic resonance signals and the first non-inversion magnetic resonance signals is carried out in between the generation of the first inversion radiofrequency pulses and in between the generation of the first non-inversion radiofrequency pulses, respectively.

Preferentially, the several first inversion radiofrequency pulses, which are used for generating an inverted blood bolus, are all in phase, wherein each of the several first inversion radiofrequency pulses rotates the magnetization a little, for instance, by about 20 to 30 degrees, until the magnetization has been inverted and thus the desired inverted blood bolus has been generated. Temporally in between these first inversion radiofrequency pulses the first inversion magnetic resonance signals are acquired. Moreover, preferentially the several first non-inversion radiofrequency pulses, which are used for generating a non-inverted blood bolus, have alternately opposite phases, i.e. a respective first non-inversion radiofrequency pulse is phase shifted by 180 degrees with respect to an immediately previous first non-inversion radiofrequency pulse. Each first non-inversion radiofrequency pulse rotates the magnetization a little, for instance, also by about 20 to 30 degrees, but temporally neighboring first non-inversion radiofrequency pulses rotate the magnetization in opposite rotational directions because of their phase shift relative to each other of 180 degrees. Thus, the effects of temporally successive first non-inversion radiofrequency pulses compensate each other with respect to the rotation of the magnetization such that a non-inverted blood bolus is obtained. Temporally in between these first non-inversion radiofrequency pulses the first non-inversion magnetic resonance signals are acquired.

The first inversion magnetic resonance signals and the first non-inversion magnetic resonance signals originate from the first region which might also be named labeling region and in which the predetermined sequences of inverted and non-inverted blood boli with inverted and non-inverted magnetization are generated by using the first inversion radiofrequency pulses and the first non-inversion radiofrequency pulses. After the predetermined sequences of inverted and non-inverted blood boli have been generated in the first region, the predetermined sequences of inverted and non-inverted blood boli flow to the part of the object to be imaged, wherein at this part of the subject to be imaged imaging magnetic resonance signals are acquired, which are used for generating a magnetic resonance image of the part of the subject to be imaged. Since the first region and the part of the subject to be imaged are different regions of the subject and since the first inversion magnetic resonance signals and the first non-inversion magnetic resonance signals originate from the first region, the first inversion magnetic resonance signals and the first non-inversion magnetic resonance signals do not originate from the part of the subject to be imaged.

Thus, the MRI system can be adapted to use a known pCASL MR sequence with additional signal readouts or ADC events. In known pCASL sequences, gradients are applied in the inter-RF spacings, which are designed to yield together with a slice-select gradient of the respective labeling pulse a mean gradient over the whole RF-RF period. The actual form of the gradient pulses does not matter as long as the integral is such that the mean net gradient is met. Therefore, any arbitrary trajectory can be applied, not only along one gradient direction, but along all (typically three) directions, i.e., for instance, along x, y and z directions. In an embodiment for pCASL preparation, i.e. for the labeling, a slice-selective Hanning-shaped RF pulse of 500 µs duration is applied about every millisecond, wherein this RF-RF interval can be called $TR_{pCASL}$. For more details regarding the known pCASL MR imaging technique reference is made to the article "Continuous flow-driven inversion for arterial spin labeling using pulsed radio frequency and gradient fields" by W. Dai et al., Magnetic Resonance in Medicine, 60(6), pages 1488 to 1497 (2008) which is herewith incorporated by reference.

It should be noted that the generation of the RF pulses, the generation of the gradients, the generation of the main magnetic field $B_0$ for initially orienting the magnetization, et cetera, i.e. that the generation of everything which influences the magnetization, is regarded as being carried out by the MR signals acquisition unit. The MR signals acquisition unit comprises several known coils and possibly further magnetic elements for generating the RF pulses, for generating the gradients, for acquiring the MR signals, et cetera.

The image generation unit is preferentially adapted to further consider the evaluation result for generating the MR image. This can lead to an improved quality of the finally generated MR image.

Preferentially, the MR signals acquisition unit is configured such that the first inversion RF pulses have the same phase and the phase of the first non-inversion RF pulses changes by 180 degrees from non-inversion RF pulse to non-inversion RF pulse. Essentially, this is identical to a steady state free precession (SSFP) sequence commonly used for MR imaging and as disclosed, for instance, in the article "Rapid gradient-echo imaging" by B. A. Hargreaves, Journal of Magnetic Resonance Imaging, 36(6), pages 1300 to 1313 (2012), which is herewith incorporated by reference. However, in pCASL a net gradient along the flow direction is applied, which might be regarded as being the z direction and which might also be the direction of the main magnetic field $B_0$ of the MR system providing the initial magnetization, wherein the net gradient is required for reliably inverting flowing spins. This residual gradient moment makes the echo train an unbalanced SSFP with partial dephasing. More details regarding this aspect are disclosed in the article "Mitigation of near-band balanced steady-state free precession through-plane flow artifacts using partial dephasing" by A. Datta et al., Magnetic Resonance in Medicine (2017) which is herewith incorporated by reference.

Moreover, preferentially the MR signals acquisition unit is constructed to acquire second MR signals being indicative of the magnetization in a second region, which is, with respect to the blood flow in the subject, downstream of the first region, by generating second RF pulses for influencing the magnetization in the second region and by acquiring second MR signals which are caused by the influence of the magnetization by the second RF pulses, wherein the evaluation unit is constructed to generate the evaluation result based on the first and second MR signals. Thus, in a variant an additional pulse can be employed to probe the longitudinal magnetization a little further downstream of the place of labeling, wherein this additional pulse can be termed ASLIF pulse. For distinguishing the first and second MR signals originating from the different first and second regions the first and second RF pulses have different frequencies and the magnetic field is different at the first and second locations, i.e. the frequencies of the first and second RF pulses correspond to the Larmor frequencies at the first and second locations, respectively, as defined by the respective magnetic field strength. The first and second RF pulses can also be regarded as being combined RF pulses having a beat due to the different frequencies, i.e. the combined RF pulse is a beat pulse. The probing by using the second RF pulses, which could be called ASLIF pulses, increases sensitivity and interpretability of the results, i.e. of the evaluation of the quality of inverting the magnetization. This additional RF pulse downstream, which allows for a more controlled excitation, does not change the timing.

Preferentially, the MR signals acquisition unit is constructed such that the distance between the first region and the second region leads to an additional phase shift of the first MR signal of 90 degrees per repetition time (TR). When using the additional ASLIF pulse, i.e. when using the second RF pulse for influencing the magnetization in the second region, a problem might arise from signal contamination from the ASL pulse, i.e. from the first RF pulse, for instance, because of different slice profiles for control and labeling states. A separation of the ASL pulse and the ASLIF pulse can be achieved by applying the two pulses at a distance which results in an additional phase shift of 90 degrees per TR, wherein this phase shift is preferentially caused by the above mentioned mean net gradient.

Moreover, preferentially the MR signals acquisition unit is constructed such that the second RF pulses have the same phase or temporally neighboring second RF pulses have a phase shift of 180 degrees. This leads to opposing phases of the ASL pulse, i.e. of the first RF pulse and hence the first MR signal, for every other TR, regardless of label or control conditions, and aligned phases of the ASLIF pulse, i.e. of the second RF pulse and hence of the second MR signal.

Moreover, the evaluation unit is preferentially adapted to add the first inversion MR signals and the second MR signals from every other TR period, thereby generating inversion combination signals, to add the first non-inversion MR signals and the second MR signals from every other TR period, thereby generating non-inversion combination signals, and to generate the evaluation result based on the combination signals. The adding procedure cancels the signal caused by the ASL pulses and increases the signal of the ASLIF pulses. Using the combination signal in which the ASL influences are cancelled can therefore lead to an improved evaluation of the inversion quality.

In a preferred embodiment the evaluation unit is configured to a) provide an inversion model for modeling a respective inversion combination signal as a combination of a tissue MR signal caused by tissue of the subject and an inversion blood MR signal caused by inverted magnetization, wherein the blood MR signal depends on a product of the inversion efficiency and a maximum possible inverted magnetization that depends on the generated magnetic field orienting the non-inverted magnetization, b) provide a non-inversion model for modeling a respective non-inversion combination signal as a combination of the tissue MR signal caused by tissue of the subject and a non-inversion blood MR signal caused by non-inverted magnetization, wherein the non-inversion blood MR signal depends on the maximally possible non-inverted magnetization that depends on the generated magnetic field orienting the non-inverted magnetization, c) determine the inversion efficiency such that deviations between i) the non-inversion combination signals and the inversion combination signals and ii) corresponding modeled signals obtained from the inversion model and the non-inversion model are reduced, particularly minimized. This allows for a very accurate determination of the inversion efficiency. Moreover, this can be done with high temporal resolution on the fly. In an embodiment the evaluation unit is configured to determine the inversion efficiency iteratively.

For determining the inversion efficiency the evaluation unit can be adapted to use a model which models the acquisition of the first inversion magnetic resonance signals and/or the acquisition of the first non-inversion magnetic resonance signals at least based on an excitation with the first inversion radio frequency pulses and/or the first non-inversion radio frequency pulses, respectively, wherein the model depends on the inversion efficiency, i.e. the model has the inversion efficiency as a fitting parameter. In this case the inversion efficiency can be determined by fitting the model to at least the acquired first inversion magnetic resonance signals and/or first non-inversion magnetic resonance signals, respectively. This fitting of the model to the acquired signals can be carried out iteratively, wherein for the iterative fitting procedure, for instance, the Marquardt-Levenberg method or the Gradient Descent method can be used. However, also other iterative fitting methods can be employed. In an embodiment the model described in the previous paragraph is used.

In an embodiment the MR signals acquisition unit is constructed to use spatially encoding gradients for increasing the spatial resolution of acquiring the first MR signals. Hence, in order to spatially resolve the evaluation not only in one direction, i.e., for instance, in the z direction, but also in other directions, i.e., for instance, the x and y directions, spatial encoding can be applied. By providing spatial encoding in two or three directions individual vessels can be separated, i.e. the evaluation can be carried out for individual vessels.

The MR signals acquisition unit can be adapted to use an arbitrarily shaped gradient between the first and, if present, second RF pulses, wherein still the inversion quality can be reliably determined, i.e. during the "inter-RF gap" the gradient can be shaped arbitrarily, especially in order to increase the spatial resolution of signal readout. In an embodiment the MR signals acquisition unit is constructed to use flow-compensation or flow-encoding for acquiring the first MR signals. This can lead to a reduction of pulsation artifacts and thereby increase the spatial resolution of signal readout.

In an embodiment the evaluation unit is configured to provide the evaluation result to the MR signals acquisition unit which is adapted to modify the acquisition of the MR signals such that the quality of inverting the magnetization is increased. Thus, the inversion quality, i.e. the labeling efficiency, can be improved by using feedback from the evaluation unit.

The MR signals acquisition unit can be configured to use a complete gap between neighboring first RF pulses for acquiring the first inverting and non-inverting MR signals. Thus, a complete "inter-RF" time can be used to acquire signal data (ADC event).

In an embodiment the MR signals acquisition unit is constructed to acquire third MR signals being indicative of the magnetization in a third region being, with respect to the blood flow in the subject, upstream of the first region by generating third RF pulses for influencing the magnetization in the third region and by acquiring MR signals which are caused by the influence of the magnetization by the third RF pulses, wherein the evaluation unit is constructed to generate the evaluation result based on the acquired first, second and third MR signals.

FIG. 1 shows schematically and exemplarily an embodiment of an MRI system 100 for generating a series of MR images of a patient 103. The MRI system 100 comprises an MR signals acquisition unit 101 for acquiring MR signals of a subject 103, wherein the MR signals acquisition unit 101 is constructed to generate a main magnetic field $B_0$ that orients the magnetization of blood within the subject 103. The MR signals acquisition unit 101 is adapted to be operated in a) an inversion state, in which first inversion RF pulses for inverting the magnetization in a first region, which is, with respect to the blood flow, upstream of the part 102 to be imaged, are generated and first inversion MR signals are acquired, which are caused by the influence on the magnetization by the first inversion RF pulses, and b) a non-inversion state in which first non-inversion RF pulses for non-inverting the magnetization in the first region are generated and first non-inversion MR signals are acquired. The generation of the first RF pulses leads to predetermined sequences of inverted and non-inverted blood boli with inverted and non-inverted, respectively, magnetization, which flow from the first region to the part 102 to be imaged. The MR signals acquisition unit 101 is further configured to acquire imaging MR signals at the part 102 to be imaged, after the sequences of inverted and non-inverted blood boli have been flowed from the first region to the part 102 to be imaged.

For generating the sequences of inverted and non-inverted boli, which can be regarded as being label and control boli, known techniques can be used. For instance, the techniques disclosed in the following publications might be used, which are herewith incorporated by reference: "Perfusion Imaging" by J. A. Detre et al., Magnetic Resonance in Medicine, volume 23, pages 37 to 45 (1992), "Magnetic resonance imaging of perfusion using spin inversion of arterial water" by D. S. Williams et al., Proceedings of the National Academy of Sciences, USA, volume 89, pages 212 to 216 (1992), "Continuous flow-driven inversion for arterial spin labeling using pulsed radio frequency and gradient fields" by W. Dai et al., Magnetic Resonance in Medicine, volume 60, issue 6, pages 1488 to 1497 (2008) and U.S. Pat. No. 8,260,396.

The MRI system 100 comprises a control and processing device 104 including a controlling unit 105 for controlling the MR signals acquisition unit 101 such that the blood boli are generated. The controlling unit 105 can also be regarded as being part of the MR signals acquisition unit 101. The processing device 104 receives input from an input device 110, like for instance a computer keyboard, a computer mouse or a touchpad etc., and yields output to an output device 111, like for instance a display to display the MR images.

The MRI system further comprises an image generation unit 106 constructed for generating an MR image of the part 102 to be imaged based on the acquired imaging MR signals and the predetermined sequences. In particular, the image generation unit 106 is adapted to generate for each sequence of label and control boli a respective MR image and to combine the generated MR images. For instance, the image generation unit 106 can be adapted to generate a combination image by combining at least two of the already generated MR images, wherein the combination image is indicative of a combination sequence of boli being indicative of a combination of the sequences of boli to which the at least two MR images correspond. The image generation unit 106 is preferentially adapted to generate a combination image by adding and/or subtracting several images from each other. For instance, after a first MR image and a second MR image have been generated, these two MR images can be subtracted from each other, in order to generate a combination image. If a first MR image, a second MR image, a third MR image and a fourth MR image should be combined, it is possible that, for instance, the first and second MR images are added to each other and that then the third MR image and the fourth MR image are subtracted from the resulting sum image. The sequences of boli of the MR images are combined correspondingly, i.e. for instance, if a first MR image and a second MR image are subtracted from each other, also the generated sequences of boli are subtracted from each other. For more details about this very well known generation of the combination images reference is made to the article "Highly efficient accelerated acquisition of perfusion inflow series by cycled arterial spin labeling" by M. Gunther, Proceedings of the 16th annual meeting of the International Society for Magnetic Resonance in Medicine, Berlin, Germany, page 380 (2007) and WO 2007/03582 A2, which are herewith incorporated by reference.

The MRI system 100 further comprises an evaluation unit 108 constructed for generating an evaluation result by evaluating the inverting of the magnetization in the first region based on the acquired first inversion and non-inversion MR signals. In this embodiment the evaluation unit 108 is constructed to determine an inversion efficiency, which can also be named labeling efficiency, as the evaluation result, wherein the inversion efficiency is indicative of the ratio of the inverted magnetization to the non-inverted magnetization behind the first region in blood flow direction.

The MRI system 100 is adapted to perform pCASL MRI, wherein the first inversion RF pulses are labeling pulses in pCASL for inverting the magnetization in the first region which could also be regarded as being a labeling region. The labeling pulses in pCASL are used to invert the magnetization of flowing hydrogen spins. At the same time they can also be viewed as excitation pulses, thus, yielding transverse magnetization, which can be measured, i.e. which results in the first MR signals. This magnetization can be utilized to evaluate the quality of inversion. The result of the evaluation is an inversion efficiency, i.e. the labeling efficiency.

Thus, the detection of the first MR signals allows the measurement of the longitudinal magnetization in a pCASL sequence at the time of labeling, i.e. at the time of applying the first inverting and non-inverting RF pulses. Therefore, labeling efficiency can be estimated with high temporal resolution and if needed spatially resolved, allowing for the estimation of, for instance, labeling efficiency in individual vessels.

The MR signals acquisition unit 101 is adapted to provide a pCASL MR sequence which acquires MR data at the time of labeling. This is done by including a signal readout, i.e. an ADC event, between single labeling pulses, i.e. in the corresponding inter-RF spacings of the pCASL MR sequence. Thus, the MRI system is adapted to use a known pCASL MR sequence with additional signal readouts or ADC events. In the used known pCASL sequence, gradients are applied in the inter-RF spacings which are designed to yield, together with a slice-select gradient of the respective labeling pulse, a mean net gradient over the whole RF-RF period. The actual form of the gradient pulses does not matter as long as the integral is such that the mean net gradient is met. Therefore, any arbitrary trajectory can be applied, not only along one gradient direction, but along all (typically three) directions, i.e., for instance, along x, y and z directions. In this embodiment, for pCASL preparation, i.e. for the labeling, a slice-selective Hanning-shaped RF pulse of 500 µs duration is applied about every millisecond, wherein this RF-RF interval can be called $TR_{pCASL}$.

The image generation unit 106 is adapted to further consider the evaluation result for generating the MR image.

The MR system is preferentially adapted to perform pCASL MR imaging. The generation of the magnetic field preferentially includes a generation of labeling pulses in pCASL for inverting the magnetization in the first region, such that the first region could also be regarded as being a labeling region. The labeling pulses in pCASL are used to invert (or not invert in the control phase) the magnetization of flowing hydrogen spins. At the same time, they can also be viewed as excitation pulses, thus, yielding transverse magnetization, which can be measured, i.e. which results in the first MR signals. This magnetization can be utilized to evaluate the quality of inversion. The result of the evaluation is preferentially an inversion efficiency, i.e. the labeling efficiency, or a measure of it. This allows monitoring of the inversion process and enables potential corrections.

Following the recommendations of the consensus of the ASL community (D. Alsop et al.: Recommended Implementation of Arterial Spin Labeled Perfusion MRI for Clinical Applications: A consensus of the ISMRM Perfusion Study Group and the European Consortium for ASL in Dementia. Magn Reson Med. 2015 January; 73(1): 102-116.), the perfusion in each voxel can be calculated for pCASL using the following formula for the cerebral blood flow (CBF):

$$CBF = \frac{6000 \cdot \lambda \cdot (SI_{control} - SI_{label}) \cdot e^{\frac{PLD}{T_{1,blood}}}}{2 \cdot \alpha \cdot T_{1,blood} \cdot SI_{PD} \cdot \left(1 - e^{-\frac{\tau}{T_{1,blood}}}\right)} \quad [\text{ml}/100 \text{ g/min}]$$

Here, $\lambda$ is the brain/blood partition coefficient in ml/g, $SI_{control}$ and $SI_{label}$ are the time-averaged signal intensities in the control and label images respectively, $T_{1,blood}$ is the longitudinal relaxation time of blood in seconds, $\alpha$ is the labeling efficiency, Sim is the signal intensity of a proton density weighted image, and $\tau$ is the label duration. The post labeling delay time PLD is the time passing between end of labeling and image acquisition. The factor of 6000 converts the units from ml/g/s to ml/(100 g)/min, which is customary in the physiological literature. Thus, by knowing the labeling efficiency, the perfusion in each voxel can be determined and hence a perfusion image can be generated having an improved quality.

The labeling efficiency a is therefore relevant for quantification of CBF.

Thus, the detection of the first MR signal preferentially allows the measurement of the longitudinal magnetization in a pCASL sequence at the time of labeling. Therefore, labeling efficiency can be estimated with high temporal resolution and if needed spatially resolved, allowing for the estimation of, for instance, labeling efficiency in individual vessels. The measurement does not add to the scan time of a pCASL experiment and in its simplest form does not add anything else but additional signal readouts. This technique can be called arterial spin labeled input function (ASLIF).

The MR signals acquisition unit 101 is configured such that the first inversion RF pulses have the same phase and the phase of the first non-inversion RF pulses changes by 180 degrees from non-inversion RF pulse to non-inversion RF pulse. Essentially, this is identical to an SSFP sequence commonly used for MR imaging. In balanced SSFP, which is often used due to its high signal-to-noise ratio, all gradients within one RF cycle (period between two RF pulses) are nulled (i.e. each integral over x, y and z gradients are each zero). However, in pCASL a net gradient along the flow direction is applied, which might be regarded as being the z direction, which might also be the direction of the main magnetic field $B_0$ of the MR system providing the initial magnetization, and the net gradient is required for reliably inverting flowing spins. This residual gradient moment makes the echo train an unbalanced SSFP (integral over z-gradient is not zero), which leads to partial dephasing of the magnetization along z. More details regarding this aspect are disclosed in the above mentioned article by A. Datta et al., Magnetic Resonance in Medicine (2017). Since the z-direction preferentially resamples the readout direction, this makes imaging challenging.

Figure 2:
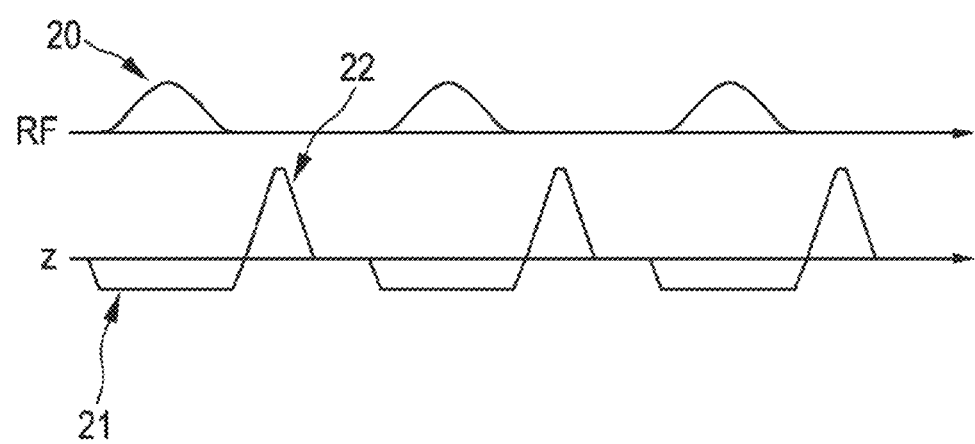
FIG. 2 illustrates exemplarily a conventional pCASL sequence.

In FIG. 2 a known MR pCASL sequence is shown, wherein in this figure reference sign 20 indicates the first inversion RF pulses used for inverting the magnetization in the first region, wherein all first inversion RF pulses have the same phase and reference signs 21, 22 indicate gradients in the z direction. Reference sign 21 denotes a slice-selection gradient to confine the effect of the first inversion RF pulse 20 to the first region, i.e. the "labeling slice". By applying the gradient 21, the magnetization is dephased along the z direction, wherein the gradient denoted by reference sign 22 rephases the magnetization along the z direction to some extent, while a certain amount of dephasing remains. This amount of dephasing corresponds to a gradient which would be constantly on during the RF cycle duration $TR_{pCASL}$ and which could also be termed as "mean net gradient $G_{ave}$". In other words, this means that at first order, the effect of the gradients denoted by reference signs 21 and 22 is identical to the effect of a mean net gradient. The mean net gradient creates an additional magnetic field which depends on the position along the z direction. For transverse magnetization located at position $z=z_1$ this additional magnetic field thus creates a phase shift $\Delta p$ relative to magnetization at position $z=z_2$ of $$\Delta p = \gamma \cdot G_{ave} \cdot (z_2 - z_1) \cdot TR_{pCASL}$$

per RF cycle, where $\gamma$ represents the gyromagnetic ratio.

Figure 3:
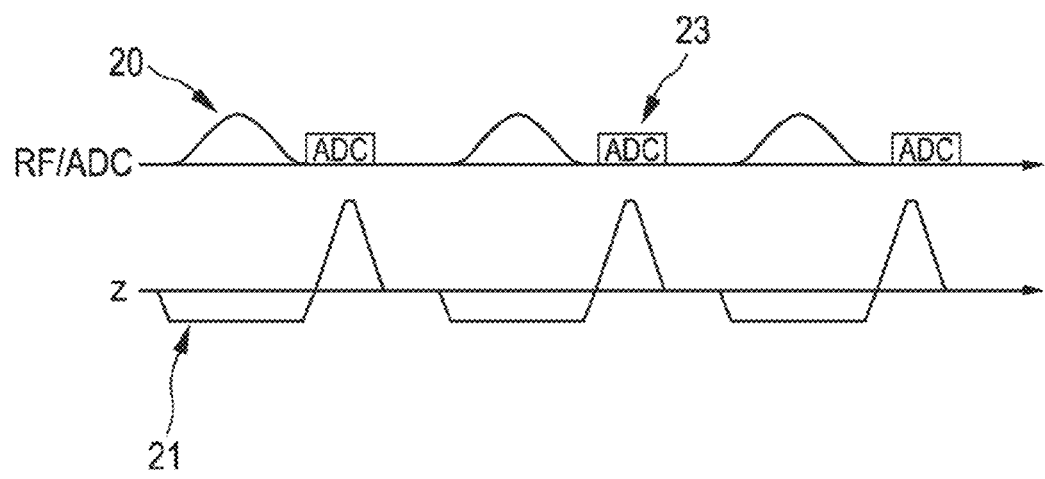
FIG. 3 illustrates exemplarily an AIF pCASL sequence.

In FIG. 3 the detection of the first MR signals, i.e. the ADC events, is indicated by the boxes 23. FIG. 3 therefore illustrates the simplest form of MR AIF pCASL. As can be seen in FIG. 3, the standard pCASL sequence shown in FIG. 2 remains almost unchanged, i.e. in this example just the signal readout 23 is added. In other words, in the simplest case just an ADC readout event 23 can be added during the rephasing gradient 22. Due to technical limitations a minimum time of 285 μs is necessary between the end of an ADC event 23 and a start of the next RF pulse 20. This basic scheme allows for a one-dimensional measurement of the labeled blood, i.e. a one-dimensional evaluation of the quality of inverting the magnetization in the first region, with a temporal resolution of, for instance, about 1 ms.

Figure 4:
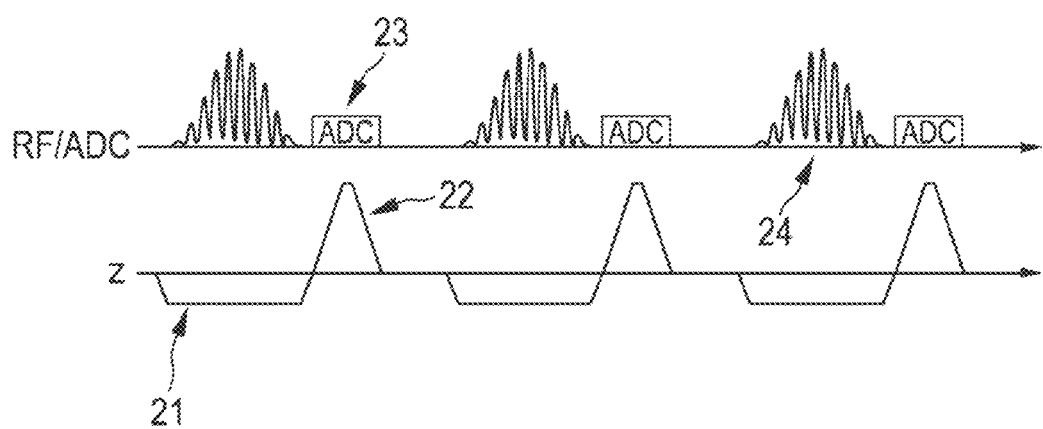
FIG. 4 illustrates exemplarily an AIF pCASL sequence with additional ASLIF pulse.

The MR signals acquisition unit 101 is constructed to acquire second MR signals being indicative of the magnetization in a second region, which is, with respect to the blood flow in the subject 103, downstream of the first region, by generating second RF pulses for influencing the magnetization in the second region and by acquiring second MR signals which are caused by the influence of the magnetization by the second RF pulses, wherein the evaluation unit 108 is constructed to generate the evaluation result based on the first and second MR signals. Thus, an additional pulse is employed to probe the longitudinal magnetization a little further downstream of the place of labeling, wherein this additional pulse is termed ASLIF pulse. For distinguishing the first and second MR signals originating from the different first and second regions the first and second RF pulses have different frequencies and the magnetic field is different at the first and second locations, i.e. the frequencies of the first and second RF pulses correspond to the Larmor frequencies at the first and second locations, respectively, as defined by the respective magnetic field strength. The first and second RF pulses are combined RF pulses having a beat due to the different frequencies, i.e. the combined RF pulse is a beat pulse 24 as schematically illustrated in the corresponding sequence shown in FIG. 4. Thus, an additional readout pulse is added, which excites a slab, i.e. the second region, downstream of the labeling slab, i.e. of the first region, which could be named ASLIF pulse and which forms, together first the ASL pulse, the combined beat pulse 24.

The MR signals acquisition unit 101 is constructed such that the distance between the first region and the second region leads to an additional phase shift of the first MR signal of 90 degrees per TR. When using the additional ASLIF pulse, i.e. when using the second RF pulse for influencing the magnetization in the second region, a problem might arise from signal contamination from the ASL pulse, i.e. from the first RF pulse, for instance, because of side bands of the pulse profiles, which are different for control and labeling states. A separation of the ASL pulse and the ASLIF pulse can be achieved by applying the two pulses at a distance which results in an additional phase shift of 90 degrees per TR, wherein this phase shift is preferentially caused by the above mentioned mean net gradient.

Moreover, the MR signals acquisition unit 101 is constructed such that the second RF pulses have the same phase or temporally neighboring second RF pulses have a phase shift of 180 degrees. This leads to opposing phases of the ASL pulse, i.e. of the first RF pulse and hence the first MR signal, for every other TR, regardless of label or control conditions, and aligned phases of the ASLIF pulse, i.e. of the second RF pulse and hence of the second MR signal. This is illustrated in FIGS. 7 and 8.

Figure 7:
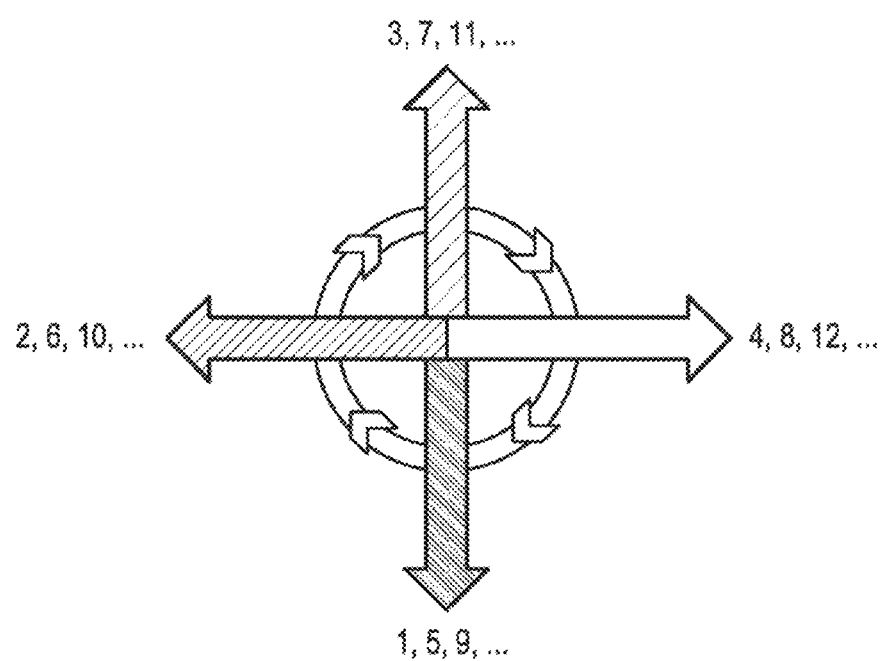
FIG. 7 shows a phase diagram exemplarily illustrating phases of ASL pulses for a label state.

FIG. 7 schematically illustrates, for a sequence of TR periods 1, 2, 3, 4, . . . , the respective phase of the ASL pulse, i.e. of the first RF pulse and hence of the first MR signal. As can be seen in this figure, the phase changes by 90 degrees from TR period to TR period in, in this example, a clockwise direction. First MR signals for every other TR period therefore have a phase difference of 180 degrees. FIG. 7 refers to the label state in which all first RF pulses initially have the same phase for all TR periods, wherein the 90 degrees phase shift is caused by the mean net gradient and the distance between the corresponding first and second regions.

The ASL pulse directly influences magnetization at the second region due to imperfect slice profile. The main problems arise from side bands influencing the static tissue spins instead of flowing spins. Thus, it is not necessary for the magnetization to flow from the first region to the second region to have an influence. Essentially, the transverse part of the magnetization of magnetization experiencing the ASL pulse at the first region will be completely dephased far before it reaches the second region due to the mean net gradient.

Figure 8:
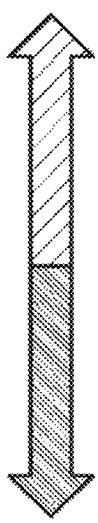
FIG. 8 shows a phase diagram exemplarily illustrating phases of ASLIF pulses with alternating sign.
Figure 9:
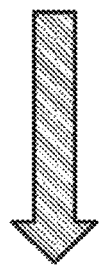
FIG. 9 shows a phase diagram exemplarily illustrating phases of ASLIF pulses for with constant sign.

FIG. 8 schematically illustrates, for a sequence of TR periods 1, 2, 3, 4, . . . , the respective phase of the ASLIF pulse, i.e. of the second RF pulse and hence of the second MR signal. As can be seen in this figure, the phase changes by 180 degrees from TR period to TR period. Thus, second MR signals for every other TR period are aligned with each other. Although in FIG. 8 the ASLIF pulses of subsequent TR periods differ by a phase of 180 degrees, in another embodiment they can also all have the same phase as schematically illustrated in FIG. 9.

Figure 10:
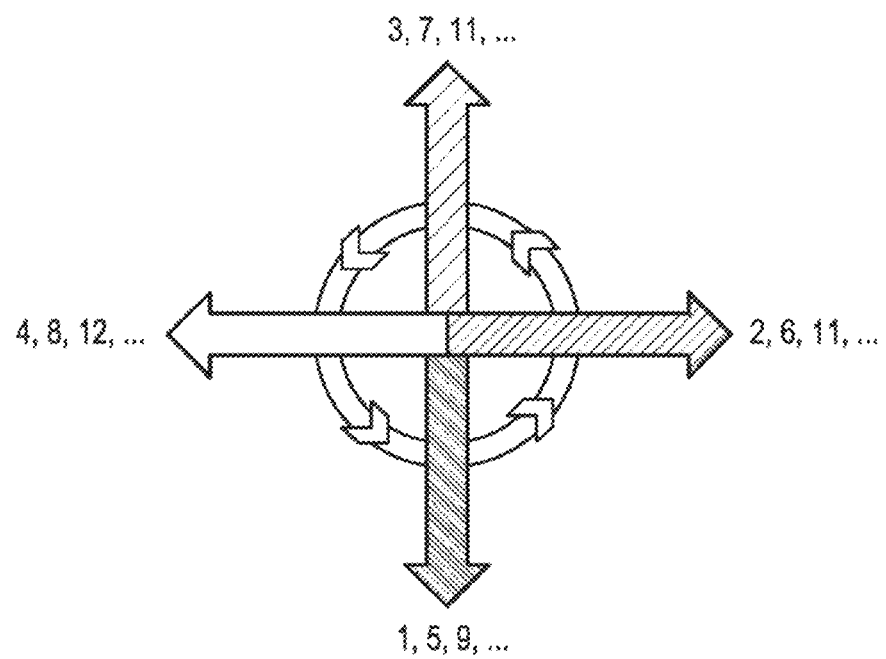
FIG. 10 shows a phase diagram exemplarily illustrating phases of ASL pulses for a control state.

FIG. 10 schematically illustrates, for a sequence of TR periods 1, 2, 3, 4, . . . , the respective phase of the ASL pulse, i.e. of the first RF pulse and hence of the first MR signal, for the control state, in which subsequent ASL pulses initially have a phase difference of 180 degrees. Due to the additional phase shift of 90 degrees from TR period to TR period, which is caused by the mean net gradient and the correspondingly chosen distance between the first and second regions, in fact the phase changes by 90 degrees from TR period to TR period in, in this example, a counter-clockwise direction. Also in this control state first MR signals for every other TR period therefore differ by 180 degrees.

The evaluation unit 108 is adapted to add the first inversion MR signals and the second MR signals from every other TR period, thereby generating inversion combination signals, to add the first non-inversion MR signals and the second MR signals from every other TR period, thereby generating non-inversion combination signals, and to generate the evaluation result based on the combination signals. Thus, the adding procedure cancels the signal caused by the ASL pulses and increases the signal of the ASLIF pulses. Then, using the combination signal, in which the ASL influences are cancelled, can lead to an improved evaluation of the inversion quality.

The RF pulses do not only influence flowing blood water spins but also static tissue spins. Since the ASL pulses are different in label and control state, the tissue spins will provide different signals for the label and the control state. Thus, the main idea of subtracting label and control data to eliminate static tissue spins (the main idea of arterial spin labeling) usually only works far away from the labeling region. But, by canceling the effect of the ASL pulses the residual signal of static spins after subtraction of label and control states can be eliminated.

Generally, subtracting (ASL) or adding (ASLIF) signals from every other TR period cancels the signals due to one pulse and increases the signals due to the other pulse. In FIGS. 7 to 10 the phase evolution of the ASL and the ASLIF pulses is shown over a cycle of several TR periods, i.e. $TR_{pCASL}$ periods. It can be nicely seen that the phase of the labeling pulse rotates clockwise with an increment of 90 degrees, while the control pulse rotates counter-clockwise with an increment of −90 degrees. At any given time, i.e. for any $TR_{pCASL}$ period, the phase of the ASL pulse is opposite for every other $TR_{pCASL}$, while for the ASLIF pulse the phase is always the same, regardless whether the ASLIF pulse is played out with constant sign (+++++) or alternating sign (+−+−+−).

The MR system 100 is preferentially configured such that the signal readout is aligned to the ASLIF pulse. This means that preferentially the current phase of the ASLIF pulse is also added to the signal readout. Thus, if the phase of the ASLIF pulse changes the measured signal will not change its phase.

The evaluation unit 108 is configured to a) provide an inversion model for modeling a respective inversion combination signal as a combination of a tissue MR signal caused by tissue of the subject 103 and an inversion blood MR signal caused by inverted magnetization, wherein the blood MR signal depends on a product of the inversion efficiency and a maximum possible inverted magnetization that depends on the generated magnetic field orienting the non-inverted magnetization, b) provide a non-inversion model for modeling a respective non-inversion combination signal as a combination of the tissue MR signal caused by tissue of the subject and a non-inversion blood MR signal caused by non-inverted magnetization, wherein the non-inversion blood MR signal depends on the maximum possible non-inverted magnetization that depends on the generated magnetic field orienting the non-inverted magnetization, c) determine the inversion efficiency such that deviations between i) the non-inversion combination signals and the inversion combination signals and ii) corresponding modeled signals obtained from the inversion model and the non-inversion model are reduced, particularly minimized. This allows for a very accurate determination of the inversion efficiency, i.e. of the labeling efficiency. Moreover, this can be done with high temporal resolution on the fly and iteratively.

In an embodiment the labeling efficiency is calculated as $$\alpha = (SI_{control} - SI_{label}) / (2 \cdot SI_{control}),$$

wherein $SI_{control}$ control and $SI_{label}$ label are, respectively, the non-inversion and inversion combination signals and it is assumed that $SI_{control}$ control represents longitudinal magnetization in thermal equilibrium, i.e. no effect of ASL pulses on blood magnetization.

Alternatively, the labeling efficiency could be estimated by comparing the slice profiles resulting from the ASL pulses, i.e. of the first inversion MR signals, with simulated slice profiles, where the labeling efficiency is known. A simulation of the Bloch equations including flow can be performed, simulating the influence of said ASL pulses, i.e. of the first inversion RF pulses, on the local magnetization. If a local magnetic field gradient is present, which distorts the local magnetic field leading to a shift in local Larmor frequency (off-resonance), the slice profiles of the ASL pulses will change their form. By simulating the inversion process of flowing spins for a range of different off-resonance frequencies and comparing the simulated slice profiles with the measured slice profiles, the inversion efficiency (which can be readily extracted from the simulation) can be estimated for the measured slice profiles.

The specific absorption rate (SAR) can be reduced by leaving pulses out, i.e., for instance, only acquire every other period or less. This can also be useful to avoid or remove stimulated echoes. The additional ASLIF pulse also means that additional RF energy has to be applied. Most part of this RF energy will be deposited in the human body. This is indicated by the SAR, for which strict legal limits apply. To avoid too high increase in SAR the number of ASLIF pulses can be reduced, e.g. only playing out the ASLIF pulse every second TR cycle. In an embodiment the signal of an ASLIF pulse is not only measured at the directly following readout, but could also be measured in the second and third readout following the original ASLIF pulse excitation. However, due to the mean net gradient, the signal will be shifted within the readout period by the additional gradient moment $G_{ave} \cdot TR_{pCASL}$ for the second and $2 \cdot G_{ave} \cdot TR_{pCASL}$ for the third readout period. These echoes will overlap and produce some imaging artifacts, but come to a steady state rather quickly. By leaving out excitation pulses, this overlap of the different echoes can be avoided. The same is true for so-called stimulated echoes, which are produced from magnetization experiencing more than one ASLIF pulse. This can lead to refocusing of magnetization and additional echoes in the readout signal. A steady state is reached rather quickly here as well.

It is not necessarily needed to subtract data acquired in labeling and control state to extract relevant information about the labeling process. Analyzing the data acquired in each, label and control state, separately will allow to extract some information about effectiveness of inversion or control. This could be done by analyzing the shape of the slice profile of the ASL pulse as described above or by modelling the signal of the ASLIF pulse, i.e. by modelling the second inversion MR signals. For the modelling, three components can be assumed to constitute the measured signal: signal arising from static tissue magnetization, signal arising from flowing blood magnetization and signal loss due to magnetization transfer. Static tissue magnetization can be estimated by repeating the ASLIF experiment with the ASL pulses switched off (only the ASLIF pulses are applied). Signal loss due to magnetization transfer can be estimated from an experiment only applying the ASL pulse in control state, i.e. applying the first non-inversion RF pulses. The signal behaviour of the individual component of static tissue with a longitudinal relaxation time of T1 can be modelled in the simplest case as a simple relaxation curves:

$$M(t)=M_0 \cdot (1-\exp(-t/T1)).$$

Figure 5:
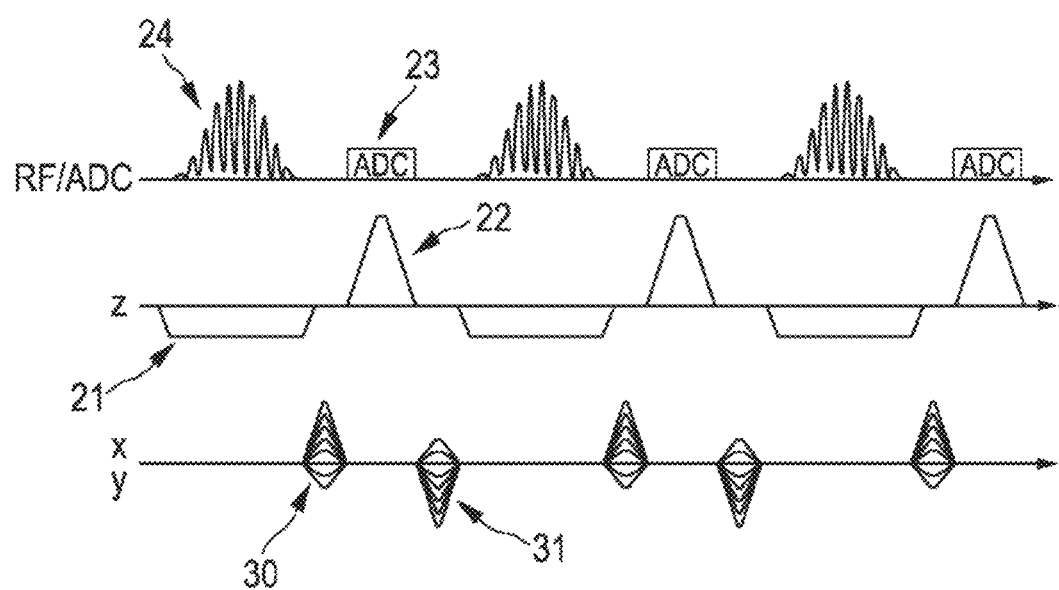
FIG. 5 illustrates exemplarily a three-dimensional variant of the AIF pCASL sequence with additional ASLIF pulse.

In an embodiment the MR signals acquisition unit 101 is constructed to use spatially encoding gradients for increasing the spatial resolution of acquiring the first MR signals. In order to spatially resolve the evaluation not only in one direction, i.e., for instance, in the z direction, but also in other directions, i.e., for instance, the x and y directions, spatially encoding can be applied as illustrated by the sequence shown in FIG. 5. By providing a spatial encoding in two or three directions individual vessels can be separated, i.e. the evaluation can be carried out for individual vessels. The gradients 30, 31 for the spatial encoding in the x and y directions are well known and disclosed in, for instance, the article "In-plane spatial encoding in MRI and its central role in determining contrast and artifact with RF echo planar techniques" by R. Mulkern, Concepts in Magnetic Resonance, volume 4, pages 307 to 325 (1992), which is herewith incorporated by reference.

The addition of the spatial gradients can be combined with parallel imaging, i.e. the MR signals acquisition unit and the image generation unit can be adapted accordingly. In parallel imaging, the imaging field-of-view is reduced so that parts of the image overlap. This saves time because less spatial information is acquired. Using the locally varying sensitivity profile of individual coils (in the brain, typically 16-32 coils are used for data acquisition), it is possible to reconstruct non-overlapping images. For more details regarding the known parallel imaging reference is made to the article "Parallel MR imaging" by A. Deshmane et al., Journal of Magnetic Resonance Imaging, 36(1), pages 55 to 72 (2012), which is herewith incorporated by reference.

Figure 6:
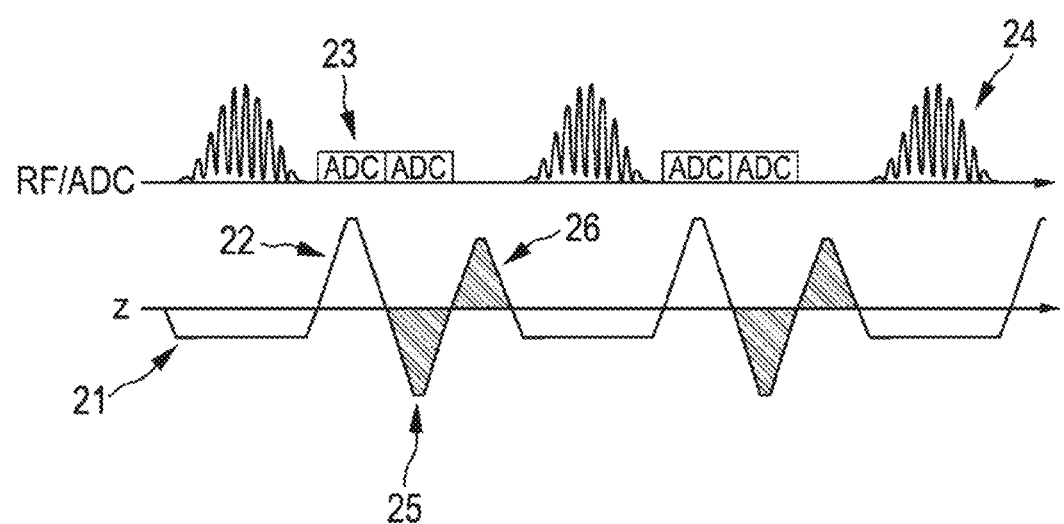
FIG. 6 illustrates exemplarily a flow-compensated AIF pCASL sequence.

Moreover, the MR signals acquisition unit 101 can be constructed to use flow-compensation or flow-encoding for detecting the first MR signals. FIG. 6 shows a sequence, i.e. a variant, with flow-compensated readout echo train which reduces pulsation artifacts. When the z-gradient waveform of the original pCASL sequence, i.e. elements 21 and 22 in FIG. 6, is used for image formation, the main signal is created at the time when the integral of the z-gradient is zero, starting from the center of element 21. However, this means that only the zeroth order of the z-gradient waveform is nulled and not the first or higher moments. The remaining first order moment means that magnetization moving at a certain velocity along z will not be fully rephased but retains a certain phase offset depending on its velocity. The given z-gradient waveform denoted by reference numbers 25 and 26 (almost) null the zeroth and the first moment at the time of the readout, thus reducing the velocity dependent phase shift and dephasing effect. For more details regarding this flow encoding technique reference is made to the article "Velocity Encoding and Flow Imaging" by M. Markl, Markl-FlowImaging.pdf, ee-classes.usc.eduiee591/library/Markl-FlowImaging.pdf (2005) and to the article "Interpretation of flow encoding and quantification in MRI: Time domain versus frequency domain" by F. Peeters et al., Magnetic Resonance in Medicine, 36(5), page 758 to 766 (1996), which are herewith incorporated by reference.

The evaluation unit 108 is also configured to provide the evaluation result to the MR signals acquisition unit 101, which is adapted to modify the acquisition of the MR signals such that the quality of inverting the magnetization is increased. Thus, the inversion quality, i.e. the labeling efficiency, can be improved by using feedback from the evaluation unit. For instance, $G_{ave}$ can be adjusted or an additional phase offset can be added to the ASL pulses and the ASLIF pulses. In order to modify additional phase offsets for ASL and ASLIF pulses independently while still retaining the fixed 180° phase coherence as described above, one of the two pulses can be slightly shifted, thus leading to a slightly different phase due to the mean net gradient.

In an embodiment the ASLIF pulse can be temporally shifted with respect to the ASL pulse. This allows additional control over the position of the echo signal. The signal of the ASLIF pulse and the ASL pulse will be maximum when the integral of the z-gradient is zero. That is called the echo position, i.e the position of the echo signal. If one of the pulses is temporally shifted, the echo position of this pulse will also be shifted.

Preferentially, the TR period is always the same, namely $TR_{pCASL}$. Even if the pulses are shifted, the period "ASL pulse to next ASL pulse" is identical to "ASLIF pulse to next ASLIF pulse".

The MR signals acquisition unit and the evaluation unit can also be adapted to measure and correct off-resonance to avoid low labeling efficiency in a single vessel or in all vessels. A linear correction gradient can be applied. By measuring the labeling efficiency with additional spatial encoding as described in FIG. 5 a spatially resolved labeling efficiency can be measured. If this varies spatially it could be corrected by using additional correction gradient pulses. For more details reference is made to the article "Pseudocontinuous Arterial Spin Labeling with Optimized Tagging Efficiency" by D. D. Shin et al., Magnetic Resonance in Medicine; 68(4), page 1135 to 1144 (2012), which is herewith incorporated by reference.

The MR signals acquisition unit 101 can be configured to use a complete gap between neighboring first RF pulses for acquiring the first inverting and non-inverting MR signals. Thus, a complete "inter-RF" time can be used to acquire signal data (ADC event). Depending on the gradient waveform this allows the acquisition of more information improving signal-to-noise as well as spatial fidelity.

Figure 11:
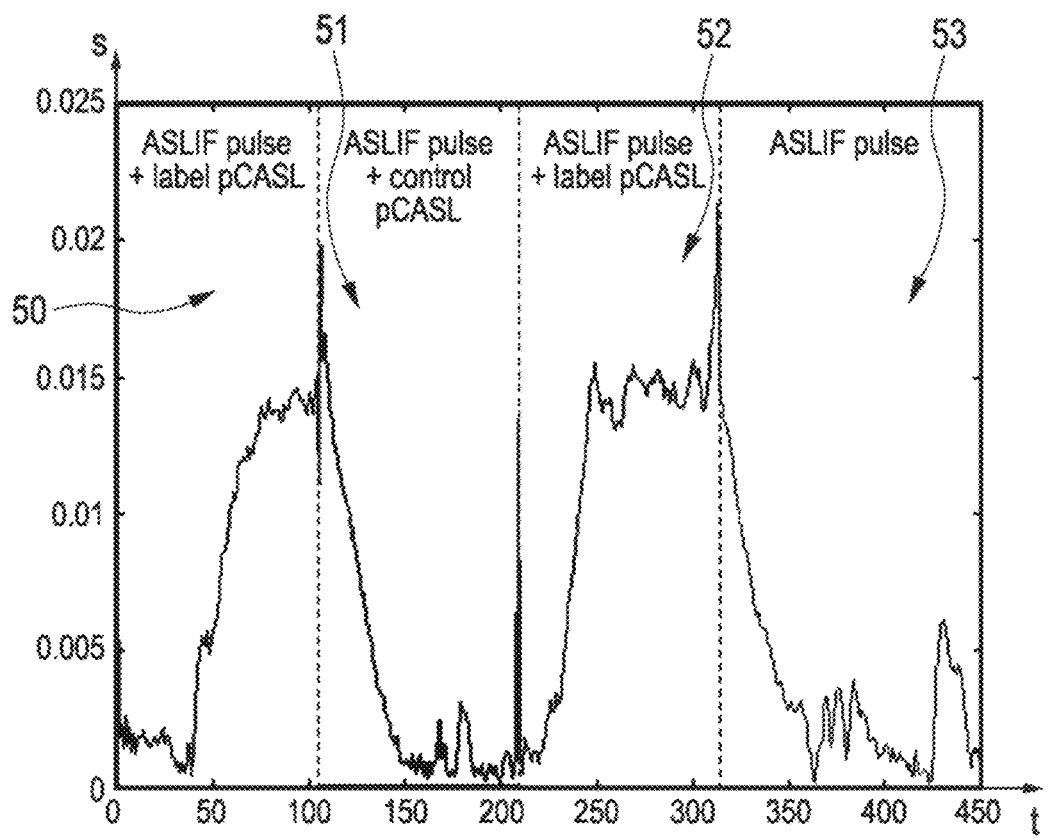
FIG. 11 shows an example of a measurement of an MR signal for different label and control states.
Figure 12:
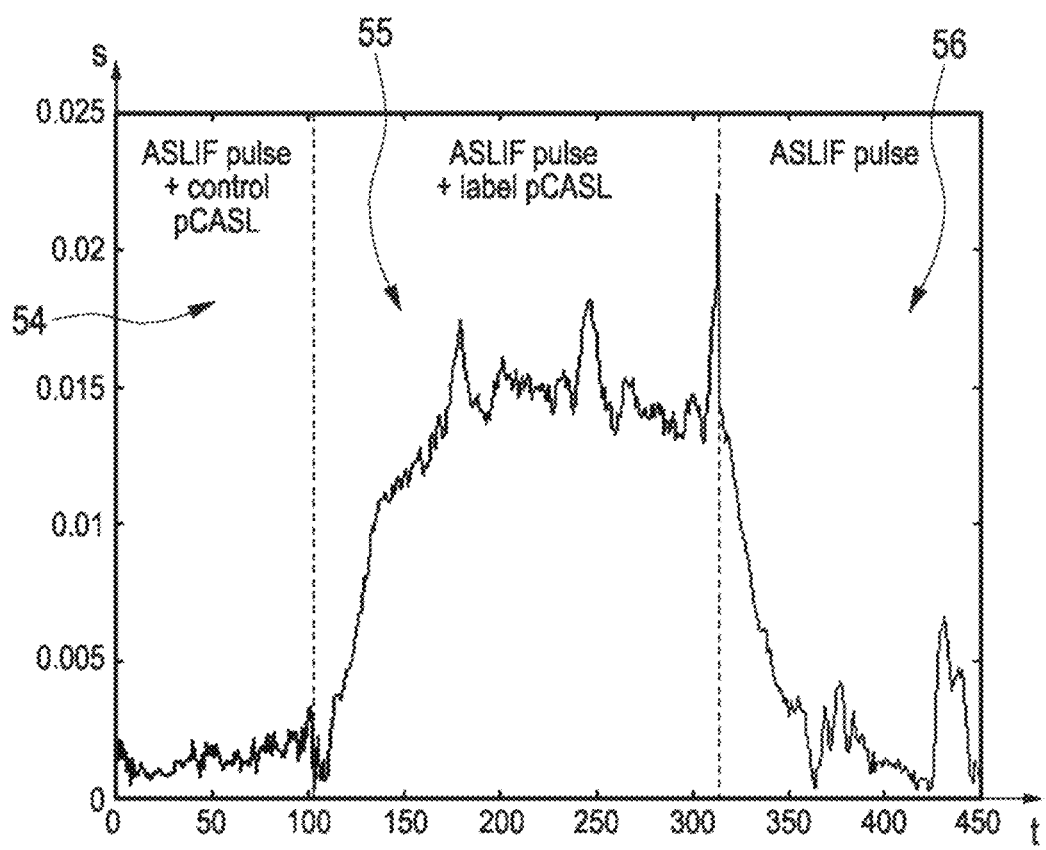
FIG. 12 shows a further example of a measurement of an MR signal for different label and control states.
Figure 13:
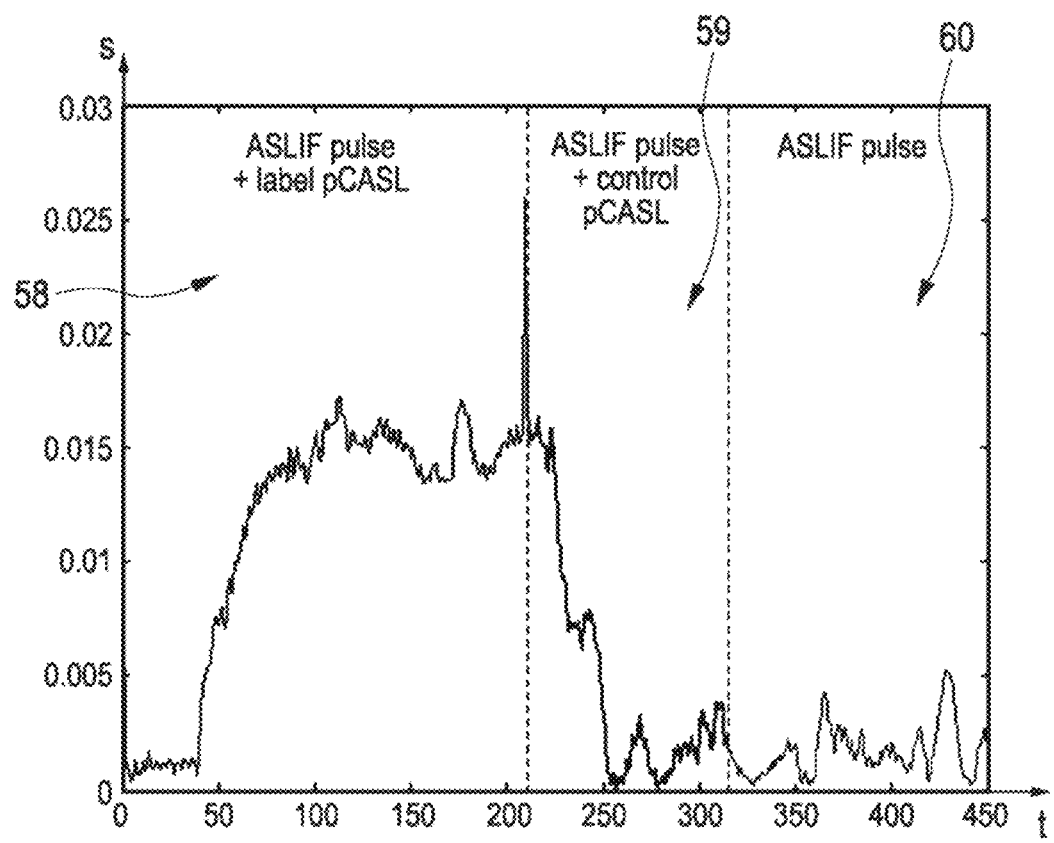
FIG. 13 shows a further example of a measurement of an MR signal for different label and control states.

Examples of signal measurements are shown in FIGS. 11 to 13. The figures depict a result of an ASLIF sequence with six phase encoding steps along the coronary direction (x-axis). A four-phase Hadamard pCASL scheme was employed. To suppress the signal from static tissue spins, the first Hadamard phase (employing control phase for all boli) was subtracted from the other three Hadamard acquisitions. The curves show the signal within the left carotid of a healthy subject, nicely depicting the labeled blood bolus with a temporal resolution of about 15 ms. The sharp peaks (not removed for educational purposes) indicate the points where cancellation of the pCASL pulse was not successful due to change of labeling/control paradigm.

In FIGS. 11 to 13 the temporal signal behavior is shown as measured with the ASLIF pulse downstream of the labeling region, i.e. downstream of the first region. Different modulations of the flowing magnetization were applied in the labeling region as indicated by the regions 50, 52, 55, 58 (during this time the flowing magnetization was inverted, i.e. labeling state) and by the regions 51, 54, 59 (the flowing magnetization was not inverted, i.e. control state). Due to the spatial distance of labeling and ASLIF region there is a delay, i.e. a shift between the indicated regions and signal rise. To separate the blood signal from the static tissue signal, a first measurement is subtracted from the shown curves, where the blood is not inverted, i.e. where the blood is in the control state. The regions 53, 56, 60 indicate periods, where no ASL pulse at all was applied.

Figure 14:
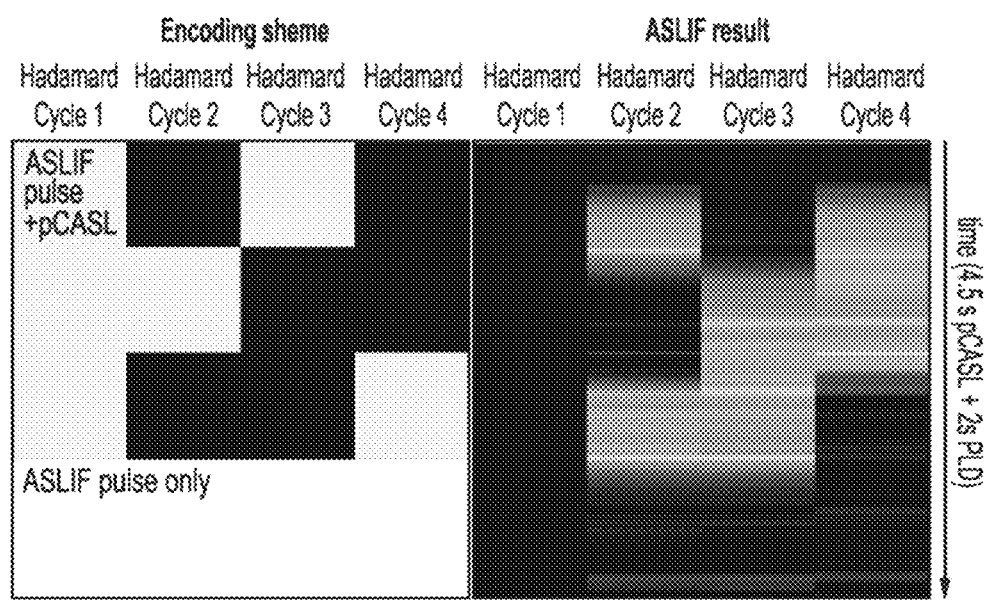
FIG. 14 illustrates different sequences of label and control boli and corresponding measured MR signals.

FIG. 14 illustrates a Hadamard-encoding matrix on the left used for labeling and a resulting labeling at the ASLIF slice on the right, i.e. in the second region, which in this example is 35 mm above the labeling slab, i.e. above the first region. In the encoding matrix, black means labeling, grey is control and white means ASLIF readout only. The time it takes the labeled blood to travel from the labeling site to the ASLIF imaging slice is nicely visualized.

FIG. 14 shows exactly the same information as FIGS. 11 to 13, but in one display. On the left side the overlay is displayed. The Hadamard cycles describe the different modulation patterns which were applied. The right side shows the curves shown in FIGS. 11 to 13 as an intensity plot.

In an embodiment the MR signals acquisition unit 101 is constructed to acquire third MR signals being indicative of the magnetization in a third region being, with respect to the blood flow in the subject, upstream of the first region by generating third RF pulses for influencing the magnetization in the third region and by acquiring MR signals which are caused by the influence of the magnetization by the third RF pulses, wherein the evaluation unit 108 is constructed to generate the evaluation result based on the acquired first, second and third MR signals. This third signal (or second ASLIF signal) measures the magnetization flowing into the labeling region. By comparing what is flowing into the labeling region and what is leaving the labeling region (with the original ASLIF pulse) the evaluation unit can directly measure the labeling efficiency.

Figure 15:
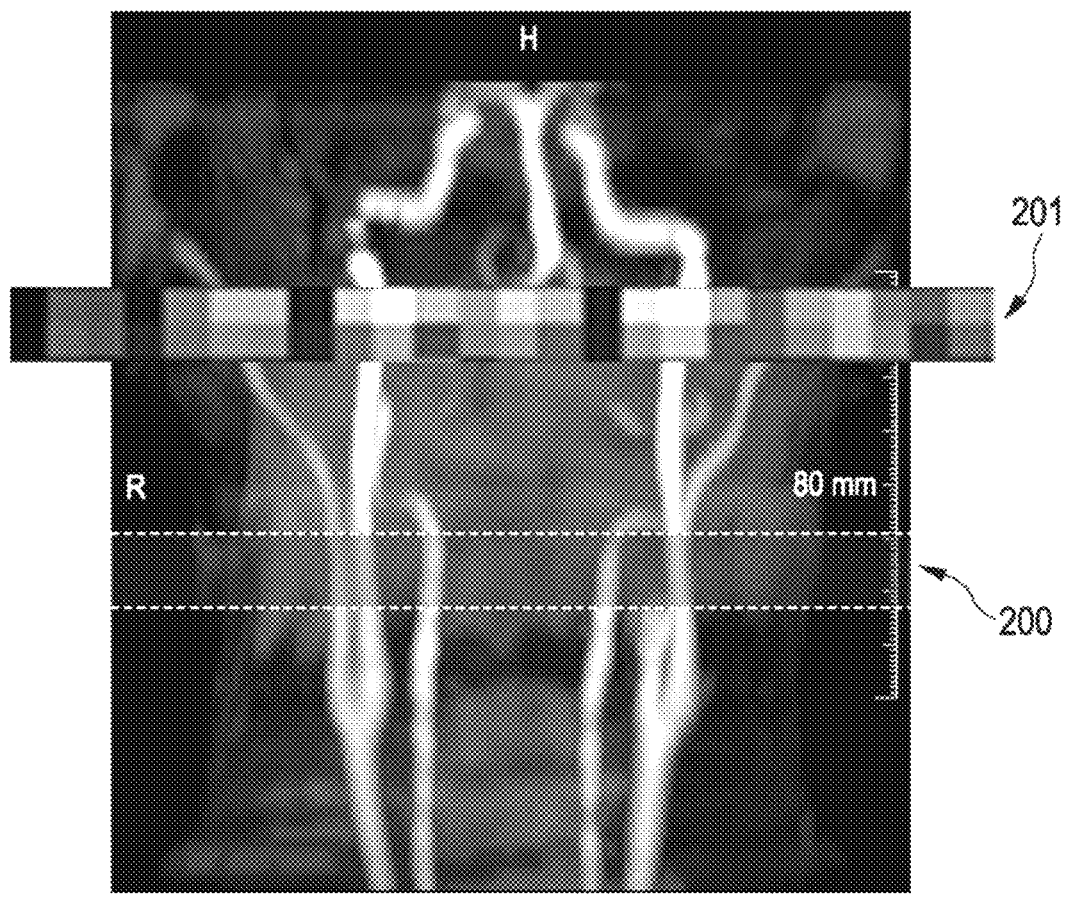
FIG. 15 illustrates a location of a first region, i.e. of a pCASL slice, and a location of a second region, i.e. of an ASLIF slice.

FIG. 15 illustrates a position of labeling, i.e. a first region 200, as well as an ASLIF slab, i.e. a second region 201, located 35 mm above the pCASL slice, i.e. above the first region 200. The difference image of the spatially resolving ASLIF sequence averaged along the time axis (12 spatial encoding steps in x-direction, partial Fourier 75 percent, reconstructed to 16 voxel) is shown nicely differentiating the individual vessels. With this setup, the labeled blood flowing through the ASLIF imaging slice, i.e. through the second region 201, can be acquired with a temporal resolution of less than 30 ms.

Other variations to the disclosed embodiments can be understood and effected by those skilled in the art in practicing the claimed invention, from a study of the drawings, the disclosure, and the dependent claims.

In the claims the word "comprising" does not exclude other elements or steps, and the indefinite article "a" or "an" does not exclude a plurality.

A single unit or device may fulfill the functions of several items recited in the claims. The mere fact that certain measurements are recited in mutually different dependent claims does not indicate that a combination of these measures cannot be used to advantage.

Procedures like the acquisition of the MR signals, the generation of the MR images, the generation of the evaluation result et cetera performed by one or several units or devices can be performed by any other number of units or devices. These procedures and/or the control of the MRI system in accordance with the MRI method can be implemented as program code means of a computer program and/or as the dedicated hardware.

A computer program may be stored/distributed on a suitable medium such as an optical storage medium or a solid state medium supplied together with or as part of other hardware, but may also be distributed in other forms, such as via the internet or other wired or wireless telecommunication systems.

Any reference signs in the claims should not be construed as limiting the scope.

The invention claimed is:

1. A magnetic resonance imaging system for generating a magnetic resonance image of a part of a subject, the magnetic resonance imaging system comprising:
   a magnetic resonance signals acquisition unit configured to acquire magnetic resonance signals of the subject, wherein the magnetic resonance signals acquisition unit is configured to:
   generate a main magnetic field that orients magnetization of blood within the subject;
   be operated in a) an inversion state, in which first inversion radio frequency pulses for inverting magnetization in a first region that is, with respect to blood flow, upstream of the part of the subject to be imaged, are generated, and b) a non-inversion state in which first non-inversion radio frequency pulses for non-inverting the magnetization in the first region are generated,
      wherein the first inversion and non-inversion radio frequency pulses are generated such that predetermined sequences of inverted and non-inverted blood boli with inverted and non-inverted, respectively, magnetization are generated in the first region, which flow from the first region to the part of the subject to be imaged,
      wherein first inversion magnetic resonance signals are acquired at the time of generating the first inversion and non-inversion radio frequency pulses and in the first region, which are caused by influence on the magnetization in the first region by the first inversion radio frequency pulses, and wherein first non-inversion magnetic resonance signals are acquired at the time of generating the first inversion and non-inversion radio frequency pulses and in the first region, which are caused by influence on the magnetization in the first region by the first non-inversion radio frequency pulses; and
   acquire imaging magnetic resonance signals at the part of the subject to be imaged, after the predetermined sequences of inverted and non-inverted blood boli have flowed from the first region to the part of the subject to be imaged;
   an image generation unit configured to generate a magnetic resonance image of the part of the subject to be imaged based on the acquired imaging magnetic resonance signals and the predetermined sequences of inverted and non-inverted blood boli; and
   an evaluation unit configured to generate an evaluation result by evaluating inverting of the magnetization in the first region based on the acquired first inversion magnetic resonance signals and/or the acquired first non-inversion magnetic resonance signals.

2. The magnetic resonance imaging system of claim 1, wherein the image generation unit is configured to further consider the evaluation result for generating the magnetic resonance image.

3. The magnetic resonance imaging system of claim 1, wherein the evaluation unit is configured to determine an inversion efficiency as the evaluation result, wherein the inversion efficiency is indicative of a ratio of the inverted magnetization to the non-inverted magnetization in the first region.

4. The magnetic resonance imaging system of claim 1, wherein the magnetic resonance signals acquisition unit is configured such that the first inversion radio frequency pulses have a same phase and the phase of the first non-inversion radio frequency pulses changes by 180 degrees from non-inversion radio frequency pulse to non-inversion radio frequency pulse.

5. The magnetic resonance imaging system of claim 4, wherein the magnetic resonance signals acquisition unit is configured to acquire second magnetic resonance signals being indicative of magnetization in a second region, which is, with respect to the blood flow in the subject, downstream of the first region, by generating second radio frequency pulses for influencing the magnetization in the second region and by acquiring second magnetic resonance signals which are caused by influence on the magnetization in the second region by the second radio frequency pulses, and wherein the evaluation unit is configured to generate the evaluation result based on the first and second magnetic resonance signals.

6. The magnetic resonance imaging system of claim 5, wherein the magnetic resonance signals acquisition unit is configured such that a distance between the first region and the second region leads to an additional phase shift of the first magnetic resonance signal of 90 degrees per repetition time (TR).

7. The magnetic resonance imaging system of claim 6, wherein the magnetic resonance signals acquisition unit is configured such that the second radio frequency pulses have a same phase or temporally neighboring second radio frequency pulses have a phase shift of 180 degrees.

8. The magnetic resonance imaging system of claim 7, wherein the evaluation unit is adapted to add the first inversion magnetic resonance signals and the second magnetic resonance signals from every other TR period, thereby generating inversion combination signals, to add the first non-inversion magnetic resonance signals and the second magnetic resonance signals from every other TR period, thereby generating non-inversion combination signals, and to generate the evaluation result based on the inversion and non-inversion combination signals.

9. The magnetic resonance imaging system of claim 8, wherein the evaluation unit is configured to a) provide an inversion model for modeling a respective inversion combination signal as a combination of a tissue magnetic resonance signal caused by tissue of the subject and an inversion blood magnetic resonance signal caused by inverted magnetization, wherein the inversion blood magnetic resonance signal depends on a product of inversion efficiency and a maximum possible inverted magnetization that depends on a generated magnetic field orienting the non-inverted magnetization, b) provide a non-inversion model for modeling a respective non-inversion combination signal as a combination of the tissue magnetic resonance signal caused by tissue of the subject and a non-inversion blood magnetic resonance signal caused by non-inverted magnetization, wherein the non-inversion blood magnetic resonance signal depends on the maximally possible non-inverted magnetization that depends on the generated magnetic field orienting the non-inverted magnetization, c) determine the inversion efficiency such that deviations between i) the non-inversion combination signals and the inversion combination signals and ii) corresponding modeled signals obtained from the inversion model and the non-inversion model are reduced.

10. The magnetic resonance imaging system of claim 3, wherein the evaluation unit is configured to determine the inversion efficiency iteratively.

11. The magnetic resonance imaging system of claim 1, wherein the magnetic resonance signals acquisition unit is configured to use spatially encoding gradients for increasing spatial resolution of acquiring first magnetic resonance signals.

12. The magnetic resonance imaging system of claim 1, wherein the magnetic resonance signals acquisition unit is configured to use flow-compensation or flow-encoding for acquiring the first magnetic resonance signals.

13. The magnetic resonance system of claim 1, wherein the evaluation unit is configured to provide the evaluation result to the magnetic resonance signals acquisition unit which is further configured to modify the acquisition of the magnetic resonance signals such that the quality of inverting the magnetization is increased.

14. The magnetic resonance imaging system of claim 1, wherein the magnetic resonance signals acquisition unit is configured to use a complete gap between neighboring first magnetic resonance pulses for acquiring the first inversion and non-inversion magnetic resonance signals.

15. The magnetic resonance imaging system of claim 1, wherein the magnetic resonance signals acquisition unit is configured to acquire third magnetic resonance signals being indicative of magnetization in a third region, being, with respect to the blood flow in the subject, upstream of the first region by generating third radio frequency pulses for influencing the magnetization in the third region and by acquiring magnetic resonance signals which are caused by influence on the magnetization in the third region by the third radio frequency pulses, wherein the evaluation unit is configured to generate the evaluation result based on the acquired first, second and third magnetic resonance signals.

16. The magnetic resonance imaging system of claim 3, wherein the evaluation unit is configured to a) provide an inversion model for modeling a respective inversion combination signal as a combination of a tissue magnetic resonance signal caused by tissue of the subject and an inversion blood magnetic resonance signal caused by inverted magnetization, wherein the inversion blood magnetic resonance signal depends on a product of inversion efficiency and a maximum possible inverted magnetization that depends on a generated magnetic field orienting the non-inverted magnetization, b) provide a non-inversion model for modeling a respective non-inversion combination signal as a combination of the tissue magnetic resonance signal caused by tissue of the subject and a non-inversion blood magnetic resonance signal caused by non-inverted magnetization, wherein the non-inversion blood magnetic resonance signal depends on the maximally possible non-inverted magnetization that depends on the generated magnetic field orienting the non-inverted magnetization, c) determine the inversion efficiency such that deviations between i) the non-inversion combination signals and the inversion combination signals and ii) corresponding modeled signals obtained from the inversion model and the non-inversion model are reduced.

17. A non-transitory computer readable memory medium containing instructions configured to control a computer processor when executed within the magnetic resonance imaging system of claim 1 to perform a method comprising:
generating a main magnetic field that orients magnetization of blood within the subject by using a magnetic resonance signals acquisition unit;
operating the magnetic resonance signals acquisition unit in a) an inversion state, in which first inversion radio frequency pulses for inverting a magnetization in a first region, which is, with respect to blood flow, upstream of the part of the subject to be imaged, are generated, and b) a non-inversion state in which first non-inversion radio frequency pulses for non-inverting the magnetization in the first region are generated, wherein the first inversion and non-inversion RF pulses are generated such that predetermined sequences of inverted and non-inverted blood boli with inverted and non-inverted, respectively, magnetization are generated in the first region, which flow from the first region to the part of the subject to be imaged, wherein first inversion magnetic resonance signals are acquired at the time of generating the first inversion and non-inversion radio frequency pulses and in the first region, which are caused by influence on the magnetization in the first region by the first inversion radio frequency pulses, and wherein first non-inversion magnetic resonance signals are acquired at the time of generating the first inversion and non-inversion radio frequency pulses and in the first region, which are caused by influence on the magnetization in the first region by the first non-inversion radio frequency pulses;

by an evaluation unit, generating an evaluation result by evaluating the inverting of the magnetization in the first region based on the acquired first inversion magnetic resonance signals and/or the acquired first non-inversion magnetic resonance signals;

by the magnetic resonance signals acquisition unit, acquiring imaging magnetic resonance signals at the part of the subject to be imaged, after the predetermined sequences of inverted and non-inverted blood boli have flowed from the first region to the part of the subject to be imaged; and by an image generation unit, generating a magnetic resonance image of the part of the subject to be imaged based on the acquired imaging magnetic resonance signals and the predetermined sequences of inverted and non-inverted blood boli.

18. A magnetic resonance imaging method for generating a magnetic resonance image of a part of a subject, the magnetic resonance imaging method comprising:

generating a main magnetic field that orients magnetization of blood within the subject by using a magnetic resonance signals acquisition unit;

operating the magnetic resonance signals acquisition unit in a) an inversion state, in which first inversion radio frequency pulses for inverting a magnetization in a first region, which is, with respect to blood flow, upstream of the part of the subject to be imaged, are generated, and b) a non-inversion state in which first non-inversion radio frequency pulses for non-inverting the magnetization in the first region are generated, wherein the first inversion and non-inversion RF pulses are generated such that predetermined sequences of inverted and non-inverted blood boli with inverted and non-inverted, respectively, magnetization are generated in the first region, which flow from the first region to the part of the subject to be imaged, wherein first inversion magnetic resonance signals are acquired at the time of generating the first inversion and non-inversion radio frequency pulses and in the first region, which are caused by influence on the magnetization in the first region by the first inversion radio frequency pulses, and wherein first non-inversion magnetic resonance signals are acquired at the time of generating the first inversion and non-inversion radio frequency pulses and in the first region, which are caused by influence on the magnetization in the first region by the first non-inversion radio frequency pulses;

by an evaluation unit, generating an evaluation result by evaluating the inverting of the magnetization in the first region based on the acquired first inversion magnetic resonance signals and/or the acquired first non-inversion magnetic resonance signals;

by the magnetic resonance signals acquisition unit, acquiring imaging magnetic resonance signals at the part of the subject to be imaged, after the predetermined sequences of inverted and non-inverted blood boli have flowed from the first region to the part of the subject to be imaged; and by an image generation unit, generating a magnetic resonance image of the part of the subject to be imaged based on the acquired imaging magnetic resonance signals and the predetermined sequences of inverted and non-inverted blood boli.

* * * * *